United States Patent [19]

Lucas

[11] Patent Number: 4,505,711
[45] Date of Patent: Mar. 19, 1985

[54] DEPOSIT DEVICE FOR DELIVERING BIOLOGICALLY ACTIVE SUBSTANCES TO THE DIGESTIVE TRACT AND METHOD OF USING SAME

[75] Inventor: Joshua M. S. Lucas, High Ongar, England

[73] Assignee: May & Baker Limited, Essex, England

[21] Appl. No.: 390,139

[22] Filed: Jun. 18, 1982

[30] Foreign Application Priority Data

Jun. 24, 1981 [GB] United Kingdom ............... 8119471

[51] Int. Cl.³ ........................... A61K 9/00; A61K 9/22
[52] U.S. Cl. ................................. 604/892; 604/890; 424/19
[58] Field of Search .............. 604/890, 892, 894, 891; 128/130; 424/19, 20, 21, 22

[56] References Cited

U.S. PATENT DOCUMENTS

| 3,056,724 | 10/1962 | Marston | 167/53 |
|---|---|---|---|
| 3,690,316 | 9/1972 | Haller | 128/130 |
| 4,249,531 | 2/1981 | Heller et al. | 604/891 |
| 4,251,506 | 2/1981 | Laby | 424/19 |
| 4,326,522 | 4/1982 | Guerrero et al. | 604/892 |
| 4,402,693 | 9/1983 | Roseman et al. | 604/890 |

FOREIGN PATENT DOCUMENTS 2059767 4/1981 United Kingdom ............... 604/892

Primary Examiner—V. Millin
Assistant Examiner—G. Beaucage
Attorney, Agent, or Firm—Stevens, Davis, Miller & Mosher

[57] ABSTRACT

A deposit device for delivering a biologically active substance to the rumen or reticulum of a ruminant comprises a cylindrical body portion, having circular flanges of rounded periphery, loaded with an active substance. The specific gravity of the loaded device should be at least 2 for retention in the stomach.

13 Claims, 1 Drawing Figure

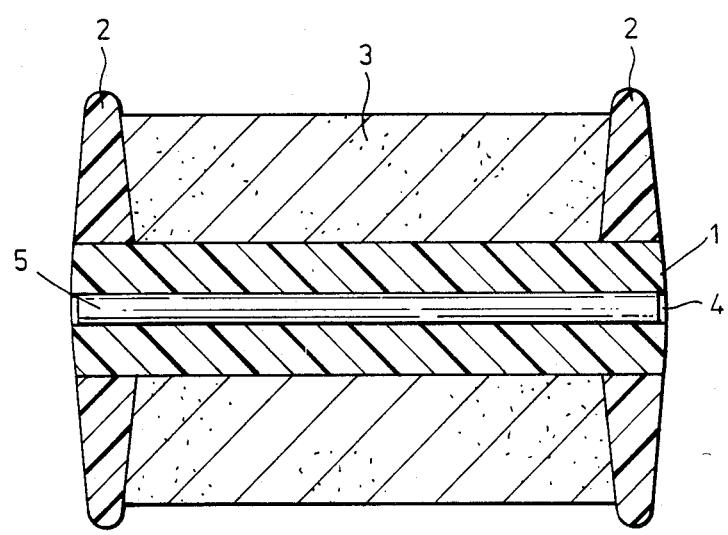

DEPOSIT DEVICE FOR DELIVERING BIOLOGICALLY ACTIVE SUBSTANCES TO THE DIGESTIVE TRACT AND METHOD OF USING SAME

The present invention relates to a deposit device for delivering a biologically active substance, for example a nutrient substance, a growth-promoting agent, an anti-parasitic agent or a therapeutic substance, to the digestive tract, and also relates to a method of administering an active substance to a ruminant.

The administration of slow-release compositions to animals is known. For example, it is known to release magmesium from a magnesium alloy "bullet" deposited in the rumen of cattle in order to allow the cattle to benefit from the activity of the magnesium.

The present invention provides a deposit device formed of a bio-compatible material, for delivering a biologically active substance to the digestive tract, comprising an elongate carrier body portion having respective flanges near its ends to define a flanged carrier body with, between the flanges, an annular space to receive a said biologically active substance; and, carried by the flanged carrier body between the said flanges, a load in the form of a mass of a biologically active substance, mounted on and around the elongate carrier body portion, the overall specific gravity of the assembly of the flanged carrier body together with its load being at least 2, and the assembly being free of sharp edges likely to cause trauma in the digestive tract of an animal.

The present invention also provides a method of delivering a biologically active substance to the rumen or reticulum of a ruminant, comprising introducing into the rumen or reticulum the above defined deposit device, and allowing the deposit device to remain in the rumen or reticulum at least until the required amount of the biologically active substance has been absorbed from the load of the deposit device.

For example, the deposit device may be intended to be retained in the rumen or reticulum of a ruminant.

The flanges not only serve to define an annular space to be occupied by the load of biologically active substance, thereby facilitating the loading of the desired amount of load onto the elongate carrier body portion, particularly when the load fills completely the annular space so-defined, but also serve, to protect the ends of the load from physical damage during handling and administration to an animal and to maintain a more constant surface area for the load during erosion of the load in the digestive tract of an animal, e.g. in the rumen or reticulum, than would be the case in the absence of the flanges.

Generally, the biologically active substance may for example comprise: a nutrient, a growth-promoting agent, an anti-parasitic agent and/or a therapeutically active substance.

More specific examples of biologically active substances include: vitamins; minerals; aminoacids; anthelmintics, e.g. thiophanate; anticoccidial agents, e.g. decoquinate; anti-microbial agents, e.g. antibiotics; hormones; antibloat agents; antihistaminics; systemic insecticides; and trace elements, e.g. cobalt, copper, manganese, molybdenum, iron, iodine, boron, vanadium and selenium.

In order that the present invention may more readily be understood the following description is given, merely by way of example, with reference to the accompanying drawing in which the sole FIGURE is a side elevational view of a first embodiment of deposit device in accordance with the present invention.

In the drawing, the deposit device comprises a substantially solid cylindrical elongate body portion 1 having at each end a radially outwardly projecting external flange 2 having a diameter at least about 3 times the diameter of the body portion 1 and with a rounded radially outer periphery. The body portion 1 and the flanges 2 are made of a biocompatible composition, for example nylon or a non-toxic metal, e.g. mild or stainless steel, so as to avoid damage to the deposit device by chemical action in the rumen or reticulum, and so as also to avoid contaminating the rumen or reticulum. The flanges 2 are non-releasably attached to the body portion 1 so as to define therebetween an annular space which, in the drawing, is occupied by a load 3 comprising a suitable active substance, either alone or in a biocompatible carrier composition, for example a wax, e.g. paraffin wax or fatty acids, e.g. palmitic acid. The load is carried solely by the flanges and the carrier body. Preferably, the cylindrical elongate body portion 1 is made of a non-toxic metal and the flanges 2 are made of nylon or the cylindrical elongate body portion 1 is made of nylon and the flanges 2 are made of a non-toxic metal, but more particularly both the cylindrical body portion 1 and the flanges 2 are made of a non-toxic metal.

As indicated above, the active substance may be a nutrient substance, or a growth-promoting substance, or a therapeutically active composition to treat some disorder of the beast.

In the embodiment of the deposit device illustrated in the drawing an axially extending through-bore 4 is formed in the cylindrical elongate body portion 1, for the purposes of receiving a supplementary component such as a pin which may be of X-ray opaque material or of a high density composition to adjust the density of the deposit device. However, the axial through-bore 4 is an optional aspect as one example of means of ensuring that the deposit has the required density, to be discussed below.

The rounded outer periphery of the flanges 2 serves to eliminate trauma in the beast when the deposit device is entering the rumen or reticulum or is at rest in the rumen or reticulum.

The deposit device illustrated in the drawing can be of various sizes. Generally the length of the device may be from 45 mm to 80 mm and the flange diameter may be from 15 to 26 mm.

One preferred form of the device, which has been used successfully in sheep, is 5 cm in overall length and has a diameter of 4 mm for the elongate body portion 1 and of 15 mm for the flanges 2, the flanges 2 each having an axial extent (thickness) of 5 mm. The empty weight of the device was approximately 11 g. and the volume approximately 2.25 ml empty.

For cattle, a successful embodiment has an overall length of 6 cm with a diameter of 4 mm for the elongate body portion 1, a thickness of 5 mm for the flanges 2, but a diameter of 22 mm for the flanges. In each case the flanged carrier body of the successful deposit device has been made of nylon and a non-toxic metal (mild or stainless steel), or of metal (mild or stainless steel) alone. An X-ray opaque pin (5 in the drawing) was inserted in certain of these flanged carrier bodies in order to identify the device when more than one had been administered to a single animal, and to observe the placement and retention of the device.

A device of the form described above intended for sheep has been used successfully in cattle, subject to the overall specific gravity of the device falling within a particular range.

In each case, the device was administered by being placed, by hand or using a balling gun, on the back of the tongue of the beast with the longitudinal axis of the elongate body portion 1 coaxial with the throat.

In tests carried out with the devices just described the following results were obtained:

|  | Wt. (g) | S.G. | Device Illustrated (empty) Lost/Retained | Control Bolus Lost/Retained |
|---|---|---|---|---|
| In sheep | 11 | 7.3 | 0/20 | |
|  | 10 | 2.7 | 0/5 | |
|  | 9 | 2.3 | 0/8 | |
|  | 8 | 2.2 | 1/5 | |
|  | 7 | 2.3 | 0/1 | |
|  | 6 | 2.0 | 3/0 | |
|  | 5 | 1.5 | 4/0 | |
|  | 4 | 1.2 | 2/0 | |
|  | 3 | 1.2 | 5/0 | |
|  | 20 | 2.5 | | 0/3 |
|  | 20 | 2.0 | | 0/4 |
|  | 20 | 1.5 | | 1/3 |
|  | 20 | 1.0 | | 2/0 |
| In calves | 16 | 2.3–2.8 | 0/3 | |
|  | 9 | 2.3 | 0/2 | |
|  | 8 | 1.1 | 2/0 | |
|  | 4 | 2.0 | 4/0 | |

The column headed "control bolus" relates to a body having a known density and a shape similar to that of the device illustrated (when loaded), and served to evaluate the density values required of the loaded device, whereas the column "device illustrated" gives the number of unloaded flanged carrier bodies lost and the number retained, respectively, for the configuration of flanged carrier body illustrated in the drawing.

From the above results, we conclude that the specific gravity of the unloaded flanged carrier body must be at least 2, preferably at least 2.2 for it to remain in the rumen. When the composition to be applied as the load 3 has a specific gravity of less than 2, added ballast may be required if the specific gravity of the flanged carrier body itself is not high enough to ensure that when initially loaded with a low specific gravity composition the overall specific gravity will still be in the required range. The specific gravities of the flanged carrier body, the load and any ballast must be such that the overall specific gravity of the device at the time of administration to the animal is at least 2, and preferably at least 2.2, and remains at least 2, and preferably at least 2.2, during the progressive erosion of the load by physical or chemical action in the rumen or reticulum.

Other tests have revealed that with exactly the same shape of deposit device, an all-nylon flanged carrier body having a relatively low specific gravity may be lost whereas a similar device having a weightening pin in its bore 4 will be retained, by virtue of the higher specific gravity of the flanged carrier body.

The flanged carrier body may be formed of any suitable material provided it is not toxic to the ruminant in which it is to be placed.

It is envisaged that any bio-compatible active substance can be administered as biologically active substance using the flanged carrier body illustrated in the drawing.

EXAMPLE I

Tests were carried out with two devices, according to the present invention, which devices had the form illustrated in the drawing. The overall length was 4.9 cm, the diameter of the cylindrical body portion 1 was 4.5 mm. The diameter of the flanges 2 was 19 mm, the flanges 2 each having an axial extent (thickness) of 3.5 mm. The body portion 1 was of steel and the flanges of nylon. The results for these devices, (hereinafter identified as Devices A and B) are given in Tables 1 and 2 below. The devices were loaded (load 3 of the drawing) with a mixture of 2 parts by weight of paraffin wax, 5 parts by weight of iron filings and 1 part by weight of the anthelmintic thiophanate [1,2-bis-(3-ethoxycarbonyl-2-thioureido)benzene], and were administered by mouth to sheep and recovered from the rumen or reticulum 9, 28 and 59 days after administration.

TABLE 1

| Device | Weight (unloaded) | Weight (loaded) | Specific Gravity (loaded) | Weight (when recovered after 9 days) |
|---|---|---|---|---|
| A | 8.36 g | 31.72 g | 2.26 | — |
| B | 8.55 g | 31.66 g | 2.4 | 30.45 g |

TABLE 2

| Device | Weight (when recovered after 28 days) | Weight (when recovered after 59 days) | Mean daily weight loss to 59 days after administration (grams per day) |
|---|---|---|---|
| A | 29.16 g | 28.58 g | 0.05 |
| B | — | 27.86 g | 0.06 |

As can be seen from the above Tables 1 and 2, in these tests, the devices A and B of the form illustrated in the drawing were retained in the rumen or reticulum of the sheep for 59 days after administration, during which time there was a slow and sustained release of the load composition at a rate of between 50 and 70 mg per day into the digestive tract of the sheep, thereby producing a sustained administration of the anthelmintic thiophanate at a rate of between about 12 and about 17 mg per day.

EXAMPLE II

Tests were carried out on nine devices (hereinafter identified as Devices C to K) according to the present invention, which devices had the form illustrated in the drawing. The overall length was 4.9 cm, the diameter of the cylindrical body portion 1 was 4.5 mm. The diameter of the flanges 2 was 19 mm, the flanges 2 each having an axial extent (thickness) of 3.5 mm. The materials of the devices were:

| Device | Body Portion | Flanges | Load |
|---|---|---|---|
| C and D | Steel | Nylon | 1 |
| E and F | Nylon | Steel | 2 |
| G to K | Steel | Steel | 2 | the Loads indicated above were:

Load 1: a mixture of 2 parts by weight of paraffin wax, 5 parts by weight of

| | -continued |
|---|---|
| | iron powder and 1 part by weight of thiophanate. |
| Load 2: | 2 parts by weight of paraffin wax, 3 parts by weight of iron powder and 5 parts by weight of thiophanate. |

The devices were administered by mouth to sheep, and subsequently recovered from the rumen or reticulum 14 to 35 days later, weighed, returned to the animal, and recovered and weighed 47 to 74 days from initial administration, as indicated in Table 3 below, in which the results of this test are given.

TABLE 3

| DEVICE | Weight (g) Unloaded Carrier Portion | Weight (g) Loaded Device | Specific gravity of Loaded Device | Weight after recovery (g) (Days after administration) | | Mean daily weight loss (mg) (Days after administration) | |
|---|---|---|---|---|---|---|---|
| C | 9.0 | 30.73 | 2.3 | 29.26 (14) | 27.93 (47) | 105 (0–14) | 59.6 (0–47) |
| D | 8.5 | 30.32 | 2.3 | 28.56 (14) | 26.42 (61) | 125.7 (0–14) | 63.9 (0–61) |
| E | 12.84 | 31.12 | 2.4 | 27.77 (35) | 24.75 (74) | 95.7 (0–35) | 86.1 (0–74) |
| F | 12.7 | 29.05 | 2.2 | 26.16 (35) | 21.94 (74) | 82.6 (0–35) | 96.08 (0–74) |
| G | 18.3 | 35.04 | 2.7 | 31.9 (33) | 29.5 (70) | 94.8 (0–33) | 79.1 (0–70) |
| H | 18.5 | 35.38 | 2.7 | 32.11 (33) | 29.52 (70) | 99.1 (0–33) | 83.7 (0–70) |
| I | 18.0 | 33.9 | 2.6 | 30.77 (33) | 27.92 (70) | 95.1 (0–33) | 85.57 (0–70) |
| J | 18.14 | 34.04 | 2.6 | 30.85 (33) | 28.04 (70) | 96.7 (0–33) | 85.7 (0–70) |
| K | 18.12 | 34.37 | 2.5 | 31.4 (33) | 28.85 (70) | 90.0 (0–33) | 78.8 (0–70) |

As can be seen from the above Table 3, in these tests, Devices C to K, of the form illustrated in the drawing, were retained in the rumen of the sheep for up to 74 days after administration, during which time there was a slow and sustained release of the load composition at a rate of between about 60 and about 125 mg per day into the digestive tract of the sheep, thereby producing a sustained administration of the anthelmintic thiophanate at a rate between about 7.5 and about 50 mg per day.

I claim:

1. A deposit device formed of a biocompatible material, for delivering a biologically active substance to the digestive tract, comprising
   (a) substantially solid elongate carrier body means;
   (b) respective external flange means near the ends of said elongate carrier body means and projecting radially outwardly therefrom to define between them an annular space to receive a said biologically active substance the ratio of flange diameter to elongate carrier body diameter being greater than about 3:1; and
   (c) carried by the elongate carrier body means in said space between said external flange means, a load comprising a mass of biologically active substance, mounted solely on and around the carrier body and carried solely by said flange means and said carrier body, the assembly of the elongate carrier body means and the load thereon has an overall specific gravity of at least 2, and wherein said assembly is free of sharp edges likely to cause trauma in the digestive tract of an animal.

2. A deposit device according to claim 1, wherein the elongate carrier body means comprises a cylindrical body.

3. A deposit device according to claim 2, wherein said respective flange means each comprise flanges which are circular when viewed along a direction parallel to the longitudinal axis of the cylindrical carrier body.

4. A deposit device according to claim 3, wherein each of said flanges, when viewed in section on a plane extending diametrically of the cylindrical carrier body, has a rounded outer profile.

5. A deposit device according to any one of claims 1 to 4, and including means defining an axially extending bore centrally of said elongate carrier body means.

6. A deposit device according to any one of claims 1 to 4, wherein the bio-compatible material include nylon.

7. A deposit device according to any one of claims 1 to 4, wherein said specific gravity of the assembly is at least 2.2.

8. A deposit device according to any one of claims 1 to 4, wherein the biologically active substance is at least one of the group comprising: a nutrient, a growth-promoting agent, an anti-parasitic agent, and a therapeutically active substance.

9. A method according to claim 1, wherein the biologically active substance is at least one of the group comprising: a nutrient, a growth-promoting agent, an anti-parasitic agent, and a therapeutically active substance.

10. A deposit device formed of a biocompatible material, for delivering a biologically active substance to the digestive tract, comprising
   (a) elongate carrier body means made of plastic;
   (b) respective external flange means near the ends of said elongate carrier body means and projecting radially outwardly therefrom to define between them an annular space to receive a said biologically active substance;
   (c) carried by the elongate carrier body means in said space between said external flange means, a load comprising a mass of a biologically active substance, mounted on and around the carrier body, wherein the assembly of the elongate carrier body means and the load thereon has an overall specific gravity of at least 2, and said assembly is free of sharp edges likely to cause trauma in the digestive tract of an animal;

(d) means defining an axially extending bore centrally of said elongate carrier body means formed of plastic, and (e) an X-ray opaque pin received in said axially extending bore.

11. A deposit device formed of a biocompatible material, for delivering a biologically active substance to the digestive tract, comprising (a) elongate carrier body means;

(b) respective external flange means near the ends of said elongate carrier body means and projecting radially outwardly therefrom to define between them an annular space to receive a said biologically active substance; and (c) carried by the elongate carrier body means in said space between said external flange means, a load comprising a mass of a biologically active substance, mounted on and around the carrier body, wherein the assembly of the elongate body means and the load thereon has an overall specific gravity of at least 2, and wherein said assembly is free of sharp edges likely to cause trauma in the digestive tract of an animal, wherein the biocompatible material is one of: mild steel and stainless steel.

12. A deposit device formed of a biocompatible material, for delivering a biologically active substance to the digestive tract, comprising (a) elongate carrier body means formed of nylon;

(b) respective external flange means near the ends of said elongate carrier body means and projecting radially outwardly therefrom to define between them an annular space to receive a said biologically active substance; and (c) carried by the elongate carrier body means in said space between said external flange means, a load comprising a mass of a biologically active substance, mounted on and around the carrier body, wherein the assembly of the elongate carrier body means and the load thereon has an overall specific gravity of at least 2, and said assembly is free of sharp edges likely to cause trauma in the digestive tract of an animal;

(d) means defining an axially extending bore centrally of the said elongate carrier body means; and (e) a pin in said bore, said pin having a specific gravity higher than that of the said elongate carrier body means.

13. A method of delivering a biologically active substance to a stomach of a ruminant, comprising the steps of (a) introducing into the stomach a deposit device formed of a bio-compatible material, for delivering an active substance to the digestive tract, said deposit device comprising (a1) elongate carrier body means;

(a2) respective external flange means near the ends of said elongate carrier body means and projecting radially outwardly therefrom to define between them an annular space to receive a said biologically active substance; and (a3) carried by the elongate carrier body means in said space between said external flange means, a load comprising a mass of a biologically active substance, mounted on and around the carrier body, wherein the assembly of the elongate carrier body means and the load thereon has an overall specific gravity of at least 2, and said assembly is free of sharp edges likely to cause trauma in the digestive tract of an animal; and (b) allowing the deposit device to remain in the stomach while at least some of the biologically active substance has been absorbed from the load of the deposit device.

* * * * *